US008801628B2

(12) United States Patent
Teschendorf

(10) Patent No.: US 8,801,628 B2
(45) Date of Patent: Aug. 12, 2014

(54) METHODS AND SYSTEMS FOR MEDICAL HOME TESTING

(75) Inventor: Lauren K. Teschendorf, St. Louis, MO (US)

(73) Assignee: Express Scripts, Inc., St. Louis, MO (US)

( * ) Notice: Subject to any disclaimer, the term of this patent is extended or adjusted under 35 U.S.C. 154(b) by 0 days.

(21) Appl. No.: 13/339,539

(22) Filed: Dec. 29, 2011

(65) Prior Publication Data

US 2013/0172778 A1 Jul. 4, 2013

(51) Int. Cl.
*A61B 10/00* (2006.01)

(52) U.S. Cl.
USPC .............. 600/569; 600/562; 600/570

(58) Field of Classification Search
USPC ........................... 600/562, 569, 570
See application file for complete search history.

(56) References Cited

U.S. PATENT DOCUMENTS

| | | | | | |
|---|---|---|---|---|---|
| 2,413,480 | A | * | 12/1946 | Winter | 604/14 |
| 2,514,665 | A | * | 7/1950 | Myller | 600/570 |
| 2,922,422 | A | * | 1/1960 | Bletzinger | 604/14 |
| 2,955,591 | A | * | 10/1960 | MacLean | 600/569 |
| 3,358,354 | A | * | 12/1967 | Voss et al. | 29/419.1 |
| 3,499,447 | A | * | 3/1970 | Skora et al. | 604/12 |
| 3,581,744 | A | * | 6/1971 | Voss et al. | 604/14 |
| 3,628,533 | A | * | 12/1971 | Loyer | 604/14 |
| 3,791,385 | A | * | 2/1974 | Davis et al. | 604/12 |
| 3,850,160 | A | | 11/1974 | Denson | |
| 3,881,464 | A | * | 5/1975 | Levene | 600/569 |
| 3,995,618 | A | * | 12/1976 | Kingsley et al. | 600/572 |
| 4,078,656 | A | * | 3/1978 | Crane et al. | 206/223 |
| 4,361,150 | A | * | 11/1982 | Voss | 604/15 |
| 4,539,180 | A | * | 9/1985 | Schwartz | 422/401 |
| 4,610,659 | A | * | 9/1986 | Friese | 604/11 |
| 4,620,548 | A | | 11/1986 | Hasselbrack | |
| 4,633,886 | A | * | 1/1987 | Bucaro, Jr. | 600/562 |
| 4,700,713 | A | * | 10/1987 | Kist | 600/569 |
| 4,862,899 | A | * | 9/1989 | Bucaro | 600/562 |

(Continued)

FOREIGN PATENT DOCUMENTS

WO 03/011144 A1 2/2003

OTHER PUBLICATIONS

Do-it-yourself PAP Smear, straightfromthedoc, http://www.straightfromthedoc.com/50226711/doityourself_pap_smear.php, Nov. 8, 2005, United Kingdom.

(Continued)

*Primary Examiner* — Rene Towa
*Assistant Examiner* — May Abouelela
(74) *Attorney, Agent, or Firm* — Husch Blackwell LLP

(57) ABSTRACT

Methods and systems for medical home testing are described. In one embodiment, the device includes a case member, a plunger member, an accumulator member and a handle member. The case member has a first distal end portion and a first proximal end portion. The first distal end portion has a distal opening and the first proximal end portion has an aperture. The plunger member is sized and configured for sliding through the aperture. The plunger member has a second distal end portion configured to slide within the case member. The accumulator member is disposed in the case member adjacent the plunger member. The accumulator member is compressed by the case member and configured for sliding through the distal opening as the plunger slides through the aperture. The handle member is attached to the accumulator member and extends through the plunger member. Other methods and systems are also described.

21 Claims, 7 Drawing Sheets

(56) References Cited

U.S. PATENT DOCUMENTS

| | | | |
|---|---|---|---|
| 4,932,417 A * | 6/1990 | Ott | 600/562 |
| 5,121,752 A | 6/1992 | Canna | |
| D331,150 S * | 11/1992 | Hartel | D4/131 |
| 5,256,571 A * | 10/1993 | Hurley et al. | 436/17 |
| 5,445,164 A * | 8/1995 | Worthen et al. | 600/572 |
| 5,531,703 A * | 7/1996 | Skwarek et al. | 604/187 |
| 5,649,902 A * | 7/1997 | Yoon | 604/1 |
| 5,792,096 A * | 8/1998 | Rentmeester et al. | 604/14 |
| 5,795,309 A * | 8/1998 | Leet et al. | 600/569 |
| 5,823,954 A * | 10/1998 | Chaffringeon | 600/367 |
| 5,919,145 A * | 7/1999 | Sahatjian | 600/572 |
| 6,024,716 A * | 2/2000 | Rejai | 604/14 |
| 6,036,658 A * | 3/2000 | Leet et al. | 600/569 |
| 6,059,735 A * | 5/2000 | Sgro | 600/569 |
| 6,143,512 A | 11/2000 | Markovic et al. | |
| 6,155,990 A * | 12/2000 | Fournier | 600/572 |
| 6,302,853 B1 * | 10/2001 | Sak | 600/569 |
| 6,346,086 B1 * | 2/2002 | Maksem et al. | 600/569 |
| 6,450,985 B1 * | 9/2002 | Schoelling et al. | 604/15 |
| 6,475,164 B2 * | 11/2002 | Gombrich et al. | 600/569 |
| 6,921,370 B2 * | 7/2005 | Zhou et al. | 600/562 |
| 7,581,899 B2 * | 9/2009 | May et al. | 401/133 |
| 2002/0068881 A1 * | 6/2002 | Kobren et al. | 600/569 |
| 2004/0137551 A1 * | 7/2004 | Markovic et al. | 435/21 |
| 2005/0277846 A1 * | 12/2005 | Chou | 600/569 |
| 2007/0208274 A1 * | 9/2007 | Ostrowski et al. | 600/573 |
| 2007/0299364 A1 * | 12/2007 | Sangha | 600/572 |
| 2008/0188769 A1 * | 8/2008 | Lu | 600/569 |
| 2009/0112148 A1 * | 4/2009 | Morrow | 604/14 |
| 2009/0275859 A1 * | 11/2009 | Kim | 600/569 |
| 2010/0305472 A1 * | 12/2010 | Larkin | 600/570 |
| 2013/0338533 A1 * | 12/2013 | Olsen | 600/569 |

OTHER PUBLICATIONS

Ling, Geraldine, DIY Cervical Cancer Test Kit, AsiaOneHealth, http://www.asiaone.com/Health/News/Story/A1Story20100506-214507.html, Jun. 4, 2010, Asia.

Foss, Kanina, Home Kit Cold Save Women's Lives, iolNews, http://www.iol.co.za/news/south-Africa/home-kit-could-save-women-s-lives-1.391026, Feb. 27, 2008, South Africa.

Cervical Cancer: Prevention and Early Detection, http//www.cancer.org/Cancer/CervicalCancer/MoreInformation/CervicalCancerPReventionandEarlyDetection/cervical-cancer-prevention-and-early-detection-toc, American Cancer Screening Guidelines.

Pap Test Alternative, WCHS ABC 8 Eyewitness News, Healthy for Life, http//www.wchstv.com/newsroom/healthyforlife/2312.shtml, Temple University research on self-administered "Pap" testing technique.

Huang, Shelley, Women Urged to Make Use of HPV Home-testing Kits, Taipei Times, http://www.taipeitimes.com/News/Taiwan/Archives/2011/05/11/2003502960, Taiwan.

Markovic, N.S. et al., The Power of the Biomarker for Cervical Cancer Control, Journal of Clinical Oncology, 2006 ASCO Annual Meeting Proceedings Part 1, vol. 24, No. 18S (Jun. 20 Supplement), 2006:11001; http://www.asco.org/ascov2/Meetings/Abstracts?&vmview=abst_detail_view&confID=40&abstract ID=32124.

* cited by examiner

US 8,801,628 B2

METHODS AND SYSTEMS FOR MEDICAL HOME TESTING

FIELD

The field relates to medical home testing; and more specifically, to cell collection within the vaginal cavity for diagnostic analysis.

BACKGROUND

A variety of diagnostic tests require the collection of cells in the vaginal cavity. Many cell collection techniques employ scraping with a probe or the like. A skilled health care provider collects the cells in a clinical setting. After cell collection, the diagnosis is performed at the clinical setting or the cells are prepared for preservation and sent to a laboratory for diagnostic analysis. The cell collection by a health care provider at a clinic is considered daunting to many women for reasons such as convenience, cost, discomfort or embarrassment. Other women do not have access to clinics and have limited or no opportunity to any diagnostic analysis.

DETAILED DESCRIPTION

Example methods and devices for medical home testing are described. In the following description, for purposes of explanation, numerous specific details are set forth in order to provide a thorough understanding of example embodiments. It will be evident, however, to one of ordinary skill in the art that embodiments of the invention may be practiced without these specific details.

Generally, a cell collection device may be obtained to collect cells needed for a diagnostic test. The cell collection device includes a case member and a plunger member that the patient may utilize to place an accumulator member proximal the cervix. After the accumulator member collects cells, the accumulator member is removed by pulling on a handle.

The accumulator member may be placed in a collection receptacle to protect and preserve collected cells. The collection receptacle, together with the accumulator member, may be hand-delivered to a laboratory or designated drop-off site, such as an office of Quest Diagnostics, Incorporated. The collection receptacle may be shipped to a laboratory or a health care provider, for example, with a transport container. The cell collection device, the collection receptacle and the transport container may be provided or offered as a kit.

As used herein, cell or cells generally refers to cellular material originating from the body and/or foreign material such as bacterial, fungal, yeast or viral microorganisms.

Figure 1:
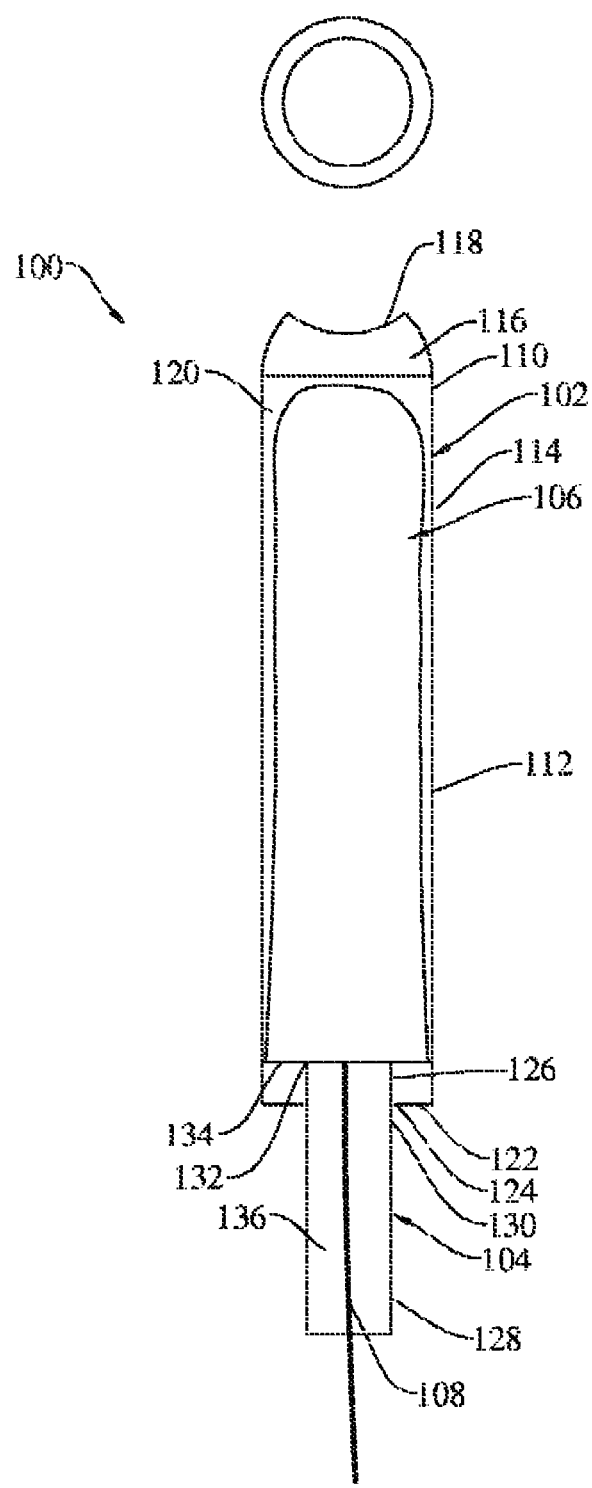
FIG. 1 is a partial cross section of a cell collection device according to an example embodiment.

Referring initially to FIG. 1, a cell collection device 100 is illustrated in accordance with a first embodiment. The cell collection device 100 includes a case member 102, a plunger member 104, an accumulator member 106, and a handle member 108. The case member 102 is slidably coupled with the plunger member 104 and houses the accumulator member 106. The plunger member 104 is configured and arranged to push the accumulator member 106 through the case member 102. The handle member 108 is attached to the accumulator member 106 and extends through the plunger member 104.

The case member 102 may be a substantially rigid member comprised of plastic polymers, for example. The case member 102 has a length that facilitates placement of the accumulator member 106. In one embodiment, the length of the case member 102 may be the length of a vaginal cavity, from the vagina to the cervix, for an average woman. The case member 102 includes a first distal end portion 110, a first proximal end portion 112, and a first sleeve portion 114 disposed between the first distal end portion 110 and the first proximal end portion 112. The first distal end portion 110 includes a first tip section 116 having a distal opening 118. In the embodiment shown in FIG. 1, the tip section 116 is frusto-conical shaped; however, the tip section 116 may be without an inclined surface. The distal opening 118 is disposed at a top section of the frusto-conically shaped tip section 116. The distal opening 118 is sized and configured for passage of the accumulator member 106. A diameter of the distal opening 118 may be smaller than a diameter of the first sleeve portion 114.

The first sleeve portion 114 is a cylindrical sleeve over the accumulator member 106. The first distal end portion 110 and the first sleeve portion 114 may include a film of petroleum gel, or similar lubricant, on an exterior. The first distal end portion 110, the first proximal end portion 112 and the first sleeve portion 114 form a cavity 120 that is sized and configured to compress the accumulator member 106 until deployment. As used herein, compress generally refers to a restricted state in which a volume of the accumulator member 106 is less than a volume of the accumulator member 106 in an unrestricted state. During deployment, the cavity 120 acts as a passage for the accumulator member 106 to slide therethrough. The first proximal end portion 112 includes an end wall 122 that partially closes the cavity 120 of the case member 102. The end wall 122 forms an aperture 124 sized and configured to receive the plunger member 104. The aperture 124 has a smaller diameter than a diameter of the first sleeve portion 114.

The plunger member 104 includes a second distal end portion 126, a second proximal end portion 128 and a second sleeve portion 130 disposed between the second distal end portion 126 and the second proximal end portion 128. The plunger member 104 is telescopically coupled with the case member 102 via the aperture 124 of the end wall 122. The second distal end portion 126 includes a second tip section 132 that is disposed within the case member 102. The end wall 122 is disposed between the second tip section 132 and the second proximal end 128. The second tip section 132 includes an outwardly extending annular flange 134. The annular flange 134 has a diameter that is larger than a diameter of the aperture 124 to prevent removal of the second tip section 132 from the cavity 120 of the case member 102.

The second distal end portion 126, the second proximal end portion 128, and the second sleeve portion 130 form a second cavity 136. The second cavity 136 provides a passage with openings for the handle member 108 to extend therethrough.

Figure 2:
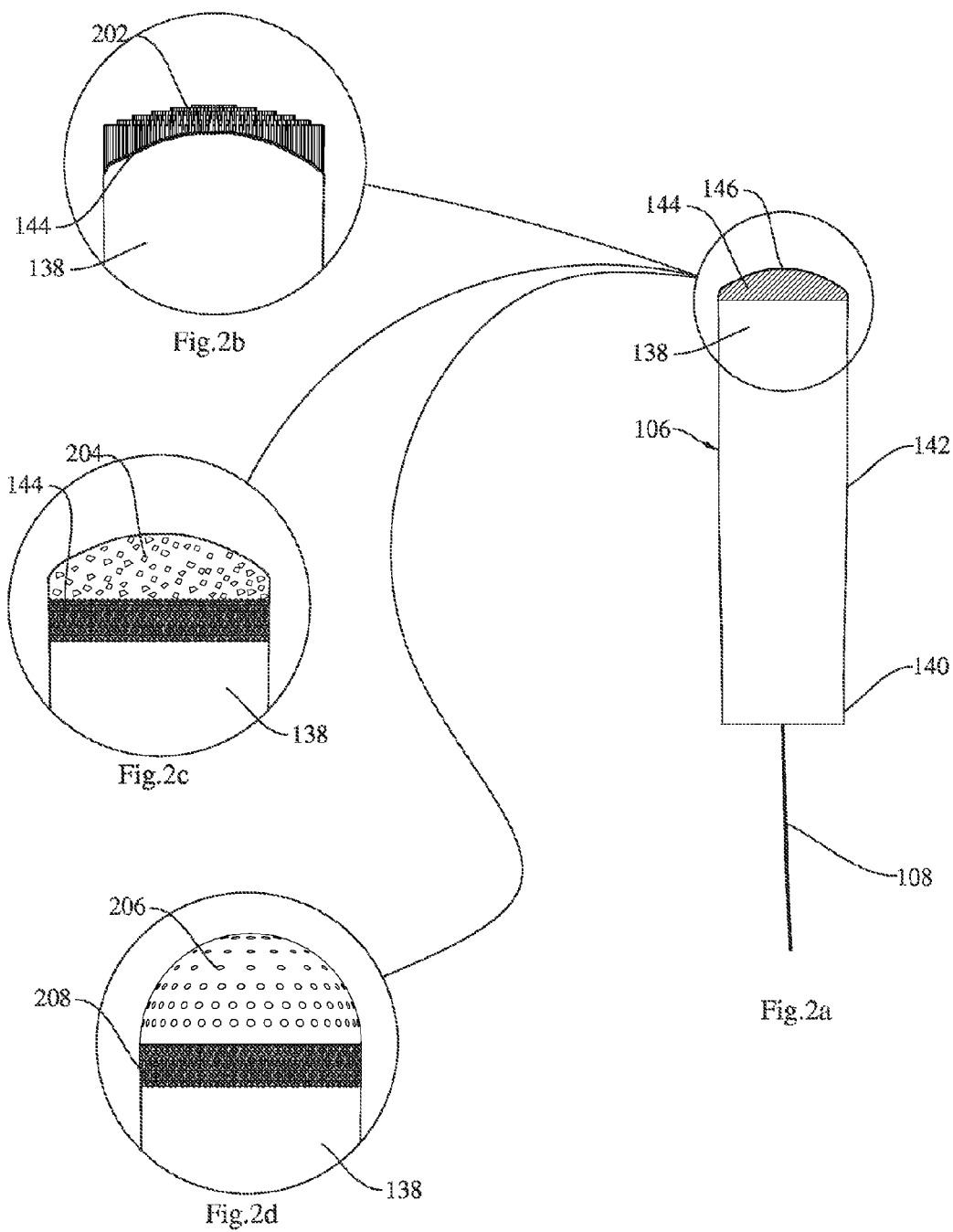
FIG. 2A is a plan view of an accumulator member of the cell collection device according to an example embodiment.
FIG. 2B is an enlarged plan view of a distal end portion of the accumulator member with microbristles according to an example embodiment.
FIG. 2C is an enlarged plan view of a distal end portion of the accumulator member with granulation according to an example embodiment.
FIG. 2D is an enlarged plan view of a distal end portion of the accumulator member with apertures according to an example embodiment.

Referring to FIG. 2A, the accumulator member 106 is illustrated in an unrestricted state according to an example embodiment. The accumulator member 106 may be composed of absorbent material such as cotton, cellulose, or combinations thereof. In some embodiments, the accumulator member 106 may comprise a synthetic sponge material. Other types of absorbent material may be used. In some embodiments, the absorbent material is sufficiently soft so as to avoid irritation during collection but yet remain sufficiently durable to collect the cells. The accumulator member 106 includes a third distal end portion 138, a third proximal end portion 140 and a body portion 142 that is disposed between the third distal end portion 138 and the third proximal end portion 140. The third distal end portion 138 includes a third tip section 144 at an end section of the accumulator member 106. The third tip section 144 may include a collection substrate 146 for cell collection and preservation. The body portion 142 may be flexible and, in some embodiments, may be porous. The body portion 142 is cylindrically shaped and may be tapered with a smaller diameter at the third proximal end portion 140 than the diameter at the third distal end portion 138. The handle member 108 may include a string or similar material attached to the third proximal end portion 140. The handle member 108 extends through the cavity 136 of the plunger member 104.

The collection substrate 146 is configured and arranged to be positioned proximal the cervix and/or contact the cervix. In some embodiments, the collection substrate 146 may be positioned at a distal exterior portion of the third tip section 144. In one embodiment, the collection substrate 146 may include a polycarbonate layer having biologically inert mixed esters of cellulose that is used for cell collection and preservation. An example of a layer of the collection substrate 146 may be a membrane filter, such as the Nucleopore™ polycarbonate membrane filter from Whatman, Ltd. The collection substrate 146 may include a polar or non-polar solvent for cell preservation.

FIGS. 2B-2D illustrate example embodiments of the collection substrate 146. Referring to FIG. 2B, a collection substrate may include microbristles 202 for engaging the cervix. The microbristles 202 aid in collection of cells by rubbing or brushing, for example, against tissue. The microbristles 202 may protect the collected cells until removal of the accumulator member 106 from the vaginal cavity. In FIG. 2C, an example embodiment of the collection substrate having granulation 204 is illustrated. The granulation 204 is for engaging the cervix and therefore aids in collection of cells. FIG. 2D illustrates the example embodiment of the collection substrate having apertures 206 for cell collection. The apertures 206 may provide a passage for cell collection at an absorptive layer 208 underneath the apertures 206.

Figure 3:
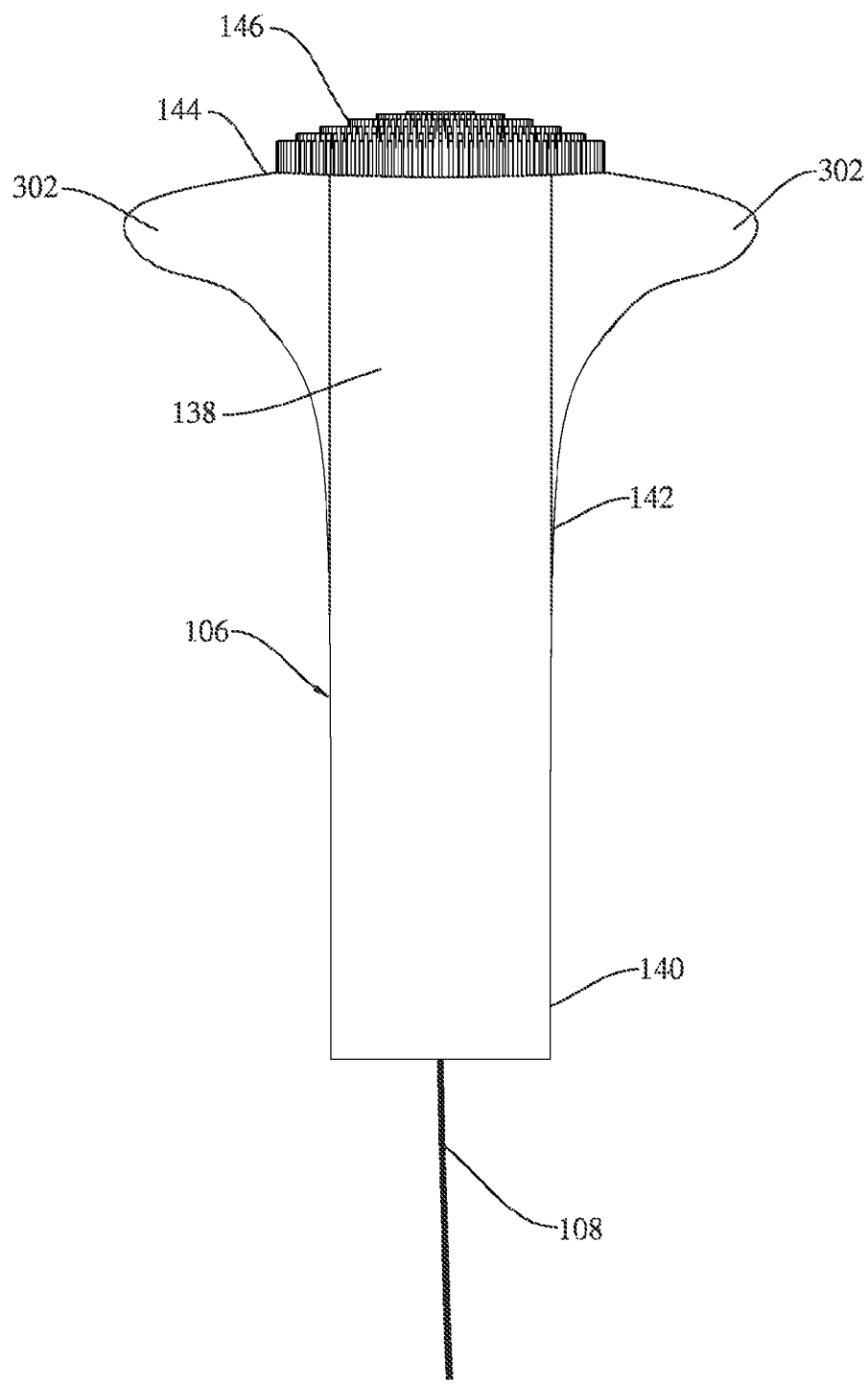
FIG. 3 is a plan view of an accumulator member having extensions according to an example embodiment.

Referring now to FIG. 3, an accumulator member 106, in accordance with an example embodiment, is disclosed. The accumulator member 106 has one or more extensions 302. A single extension 302 or multiple extensions 302 may be included as part of the accumulator member 106. The extensions 302 may expand surface area of the accumulator member 106 for stabilization of the third distal end portion 138 proximal the cervix. The extensions 302 extend outwardly from the third distal end portion 138 and are shaped in a wing-like fashion. The extensions 302 may be composed of the same or different absorbent material as the accumulator member 106. In some embodiments, the extension 302 may be made of dry natural rubber, such as that employed in a diaphragm made by Ortho-McNeil Pharmaceutical, Inc. of Raritan, N.J. The extensions 302 may be compressed within the cavity 120 of the case member 102 and expand when the accumulator member 106 is pushed through the distal opening 118. The extensions 302 may also have a spring-like structure therein to provide flexibility, but yet cause sufficient rigidity for stabilization proximal to the cervix.

The collection substrate 146 may be positioned at a distal exterior portion of the extension 302. That is, the collection substrate 146 may extend outwardly from the third tip section 144 onto the distal exterior portion of the extension 302.

Figure 4:
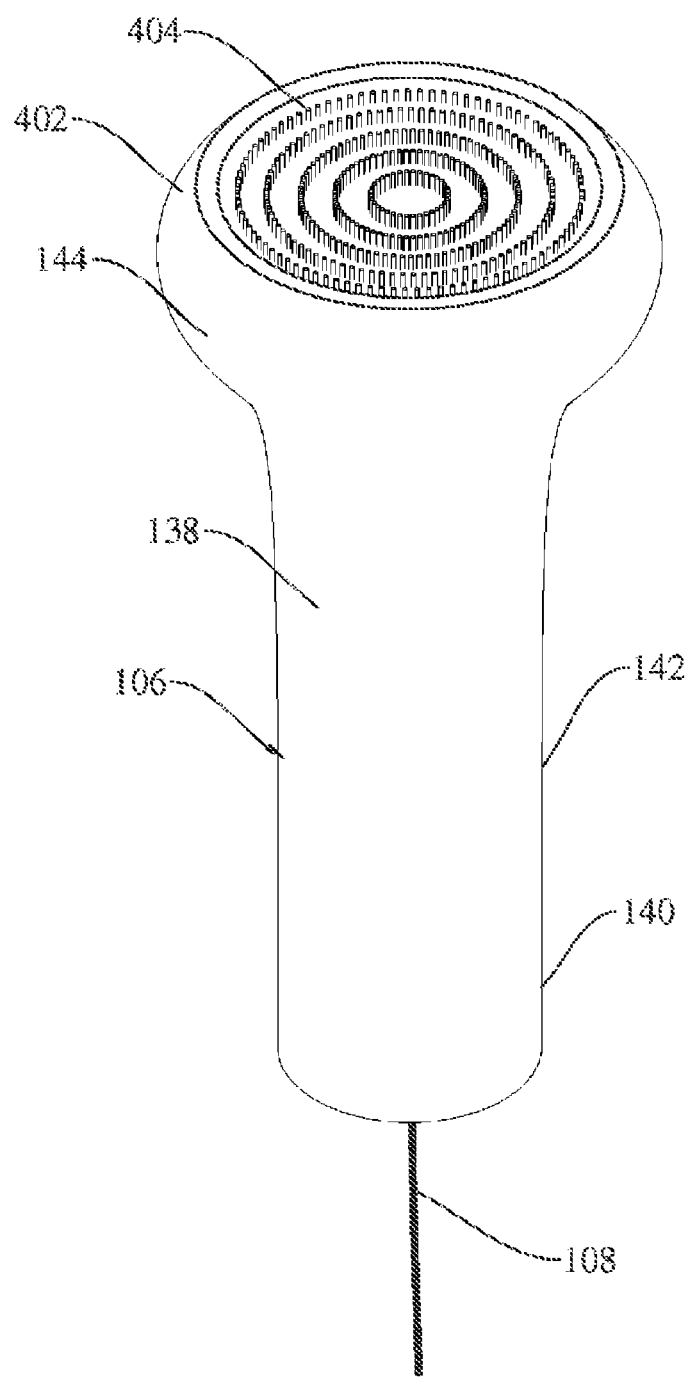
FIG. 4 is a plan view of an accumulator member having an annular extension according to an example embodiment.

In the embodiment of FIG. 4, an extension 402 is illustrated that substantially surrounds the third distal end portion 138. Specifically, the extension 402 is an annular extension configured to at least partially surround the mouth of the cervix. The extension 402 may distally extend a distance past the collection substrate 146 to extend past the mouth of the cervix. The extension 402 may be sized so that a portion of the extension 402 may be placed between the upper edge of the pubic bone and the cervix; a portion of the extension 402 may be placed between the rear wall of the vagina and the cervix. The collection substrate 146 is positioned at a distal exterior portion of the third tip section 144 in at least a portion of an area surrounded by the annular extension 402.

Figure 5:
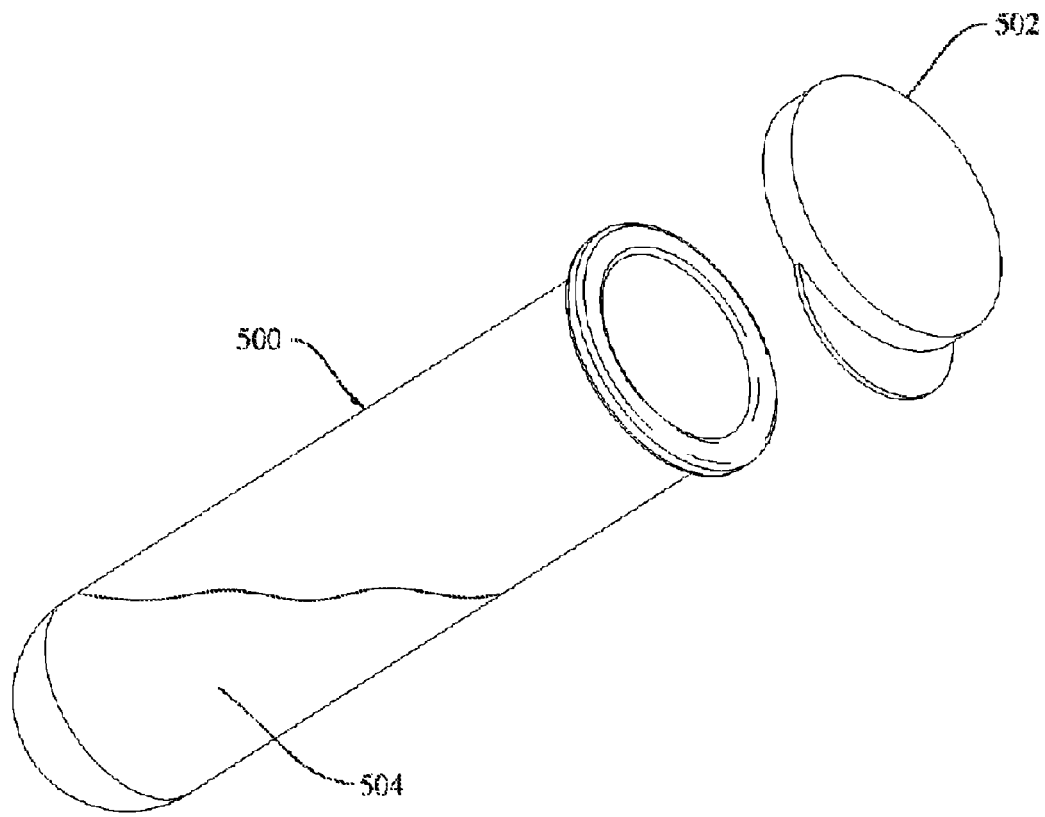
FIG. 5 is a perspective view of a collection receptacle according to an example embodiment.

Referring to FIG. 5, a collection receptacle 500 is disclosed. The collection receptacle 500 is sized and configured to receive the accumulator member 106. The collection receptacle 500 may be a rigid member comprised of polypropylene, for example. The collection receptacle 500 may be a tubular receptacle with an interior sized to receive the accumulator member 106 with minimal or no compression. A cap member 502 may be placed over an open end of the collection receptacle 500 to contain the accumulator member 106 and/or a preservation fluid 504. The cap member 502 may be snapped or screwed onto the collection receptacle 500. The preservation fluid 504 may be a solution for preserving the collected cells. Examples of the preservation fluid 504 include denatured 95% ethyl alcohol. However, other types of preservations fluids may also be used.

Figure 6:
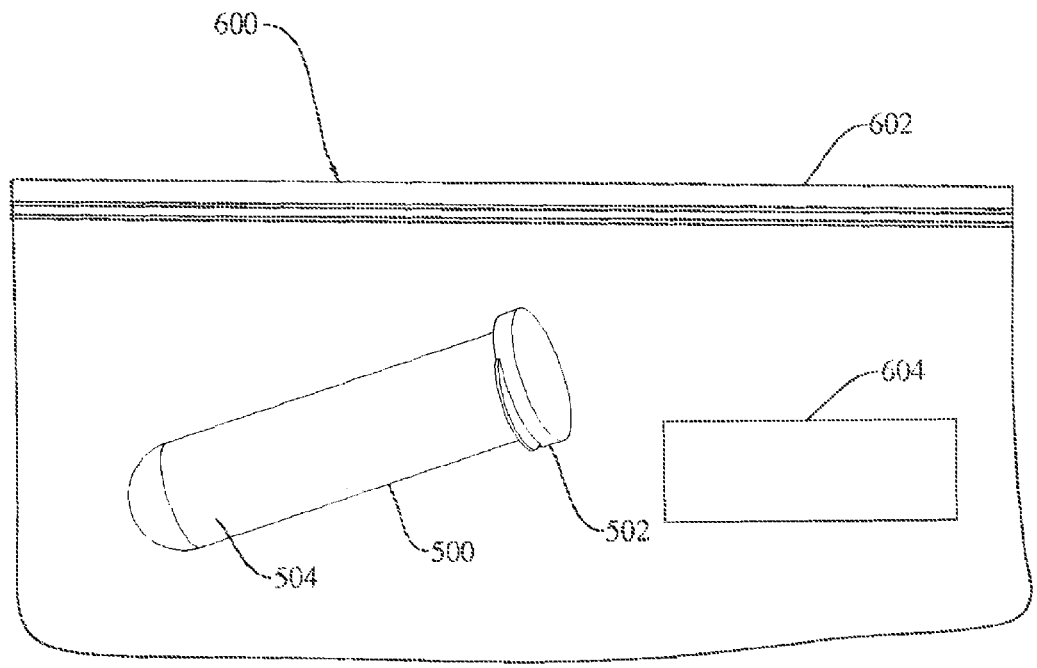
FIG. 6 illustrates a kit according to an example embodiment.

Referring to FIG. 6, a kit 600 is disclosed, according to an example embodiment. The kit 600 may include the cell collection device 100 (see FIG. 1), the collection receptacle 500 (see FIG. 5), and a transport container 602. The transport container 602 has an interior for retaining the collection receptacle 500 with the accumulator member 106 during shipment. The transport container 602 may include a label 604 on an exterior that is pre-addressed for a laboratory or health care provider, for example. The transport container 602 may be sealed for shipping using an adhesive and/or a ziplock mechanism. The adhesive may be moisture-activated or have a removable protective layer thereon. The transport container 602 may be composed of plastic, paper or a combination thereof. A protective film to shield the collection receptacle 500 from light may be included in the transport container 602.

Figure 7:
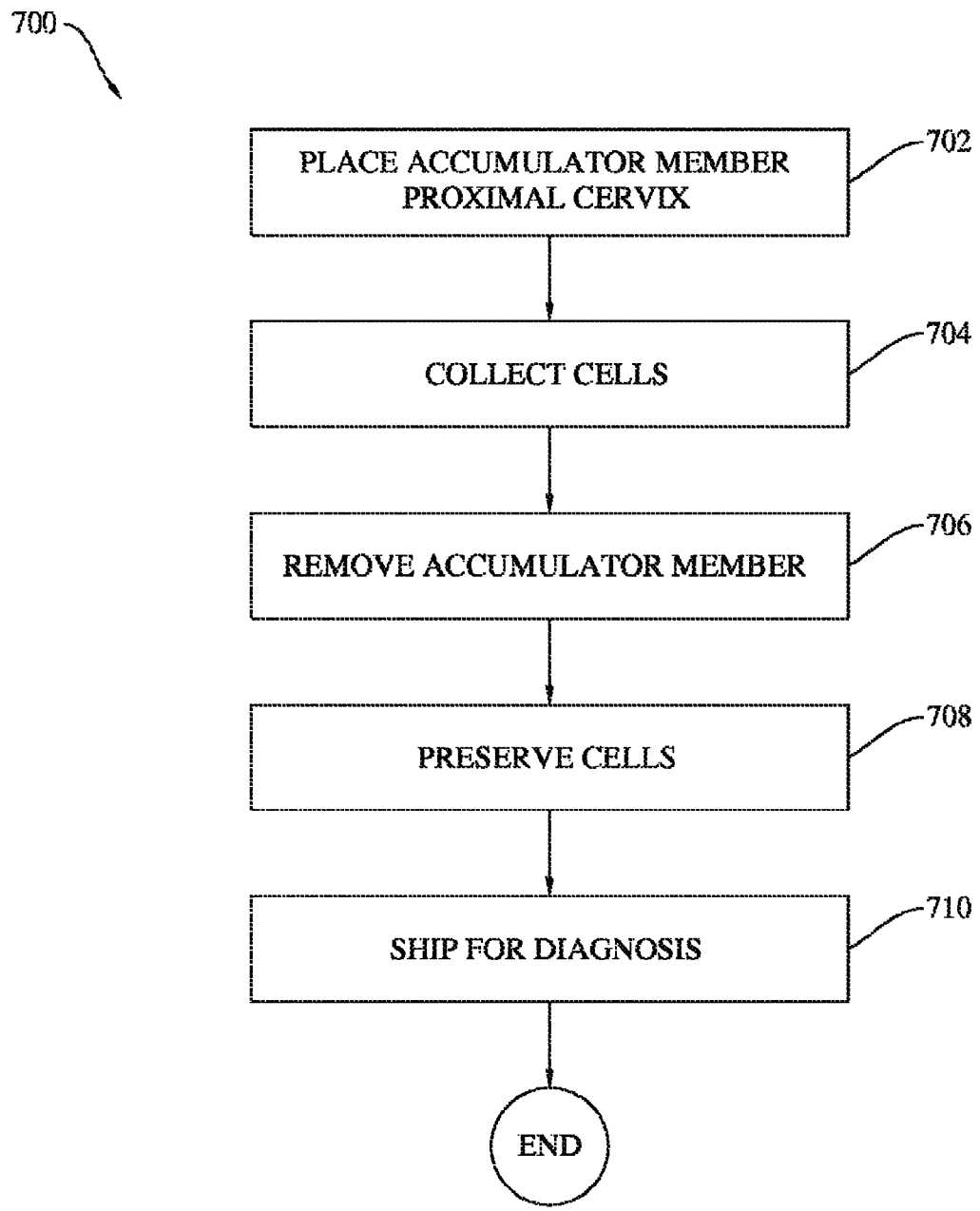
FIG. 7 is a block diagram of a flow chart illustrating a method for cell collection according to an example embodiment.

FIG. 7 illustrates a method 700 for cell collection, according to an example embodiment. The method 700 may be performed by the patient herself, or a person on behalf of the patient such as a caregiver.

The patient (or person acting on behalf of the patient) may obtain the cell collection device 100 in many different ways. An unused kit 600 may be mailed to a patient that is a member of a pharmacy benefit plan or health benefit plan, for example.

In other embodiments, the patient may purchase the kit 600 over-the-counter at a health care provider or retail store. In still other embodiments, the kit 600 may be handed out to a multitude of patients at, for example, a women's clinic in an impoverished location.

At block 702, the patient places the accumulator member 106 proximal the cervix. The accumulator member 106 may be placed proximal the cervix by inserting at least a portion of the case member 102 into the vaginal cavity. The plunger member 104 is pushed to force the accumulator member 106 through the case member 102 and its distal opening 118. The previously compressed accumulator member 106 may expand. Referring to FIGS. 3 and 4, the extensions 302, 402 of the accumulator member 106 may expand. As the case member 102 and the plunger member 104 are separated from the accumulator member 106, the handle member 108 slides through both cavities 120, 136 to remain with the accumulator member 106 in the vaginal cavity.

At block 704, collection of cells occurs. The accumulator member 106 may collect cells from cervical tissue, vaginal fluid, vaginal wall tissue, or otherwise for diagnostic testing purposes. The diagnostic test may include tests for human papilloma virus, cervical cancer, conditions leading to cervical cancer, bacterial infection, fungal infection, yeast infection, viral infection, venereal disease, or the like. In the case of collecting cervical tissue, the accumulator member 106 may passively collect cells by placement proximal the cervix. The accumulator member 106 may collect cells by rubbing or brushing up against the cervix with the collection substrate 146. The accumulator member 106 is not intended for active scraping of the cervix with a patient or physician holding onto the third proximal end portion 140.

The patient may leave the accumulator member 106 in the vaginal cavity for a determined period of time. The determined period of time may be approximately 1-4 hours or, in some cases, approximately 4-8 hours, for example. Other periods of time that are shorter or longer may also be acceptable for sufficient collection for testing purposes. The patient may perform relatively normal activities with the accumulator member 106 in place during this period of time. At block 706, the patient removes the accumulator member 106 from the vaginal cavity by pulling on the handle member 108. The cells that were collected by the accumulator member 106 are preserved at block 708. The accumulator member 106 is placed in the collection receptacle 500 and sealed therein with the cap member 502. The collection substrate 146 may be exposed to preservation fluid 504 in the collection receptacle 500.

The transport container 602 may enclose the collection receptacle 500 during shipment. At block 710, the collection receptacle 500, with the accumulator member 106 therein, is dropped off, shipped or otherwise provided to a laboratory or other health care provider for diagnostic analysis. The patient may ship the sealed transport container 602 (with the collection receptacle 500 and accumulator member 106 therein) to the address on the pre-addressed label 604.

In understanding the scope of the present disclosure, the term "configured" as used herein to describe a member, portion, section or part of a device refers to structure for carrying out the desired function. In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

In an example embodiment, an apparatus includes a case member, a plunger member, an accumulator member and a handle member. The case member has a first distal end portion and a first proximal end portion. The first distal end portion has a distal opening and the first proximal end portion has an aperture. The plunger member is sized and configured for sliding through the aperture. The plunger member has a second distal end portion configured to slide within the case member. The accumulator member is disposed in the case member adjacent the plunger member. The accumulator member is compressed by the case member and configured for sliding through the distal opening as the plunger slides through the aperture. The handle member is attached to the accumulator member and extends through the plunger member.

In an example embodiment, an accumulator member is placed proximal a cervix. Cells are collected without scraping. The accumulator member is removed. The cells in a collection receptacle are preserved. The cells are shipped in the collection receptacle.

Thus, methods and systems for medical home testing have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

The invention claimed is:

1. An apparatus comprising: a case member having a first distal end portion and a first proximal end portion, the first distal end portion having a distal opening, and the first proximal end portion having an aperture; a plunger member sized and configured for sliding through the aperture, the plunger member having a second distal end portion configured to slide within the case member; an accumulator member disposed in the case member adjacent the plunger member, the accumulator member being compressed by the case member and configured for sliding through the distal opening as the plunger member slides through the aperture to enable expansion of the accumulator member and placement of the accumulator member within a vaginal cavity and proximal to a cervix of a patient, the accumulator member comprising absorbent material, a third distal end portion including a frusto-conical shaped tip section, and a third tip section having a collection substrate at the third distal end portion to enable collection of cells in multiple zones during regular activity of the patient while accumulator member is in the vaginal cavity without active scraping by external manipulation of the accumulator member, wherein the frusto-conical shaped tip section of the third distal end portion maintains the frusto-conical shape when positioned in the case member and outside the case member; and a flexible handle member attached to the accumulator member and extending through the plunger member to remove the accumulator member from the vaginal cavity after the collection of the cells, wherein the third tip section of the accumulator member emerges from the frusto-conical shaped tip section and a part of the accumulator is retained in the case member by the frusto-conical shaped tip section when the accumulator is engaged by the plunger member.

2. The apparatus of claim 1, wherein the collection substrate includes a layer with collection apertures, microbristles, granulation, or combinations thereof.

3. The apparatus of claim 1, wherein the collection substrate includes a solution for preserving the cells after collection.

4. The apparatus of claim 1, wherein the accumulator member includes an extension extending from the third distal end portion to provide stabilization of the accumulator member while within the vaginal cavity.

5. The apparatus of claim 4, wherein the extension has a wing-like shape.

6. The apparatus of claim 4, wherein the extension extends annularly around the third distal end portion.

7. The apparatus of claim 1, wherein the first distal end portion includes a frusto-conical shaped tip section, wherein the third tip section of the accumulator member includes a first part that emerges from the frusto-conical shaped tip section and is a second part that is retained in the case member by the frusto-conical shaped tip section when the accumulator is engaged by the plunger member.

8. The apparatus of claim 7, wherein the first distal end portion is rigid.

9. The apparatus of claim 1, wherein the accumulator member further includes a flexible body portion that is cylindrically shaped and tapered with a smaller diameter at a third proximal end portion than the diameter at the third distal end portion.

10. The apparatus of claim 9, wherein the flexible body portion of the accumulator member is of a different material type than the collection substrate, and the collection of cells occurs in the multiple zones via the flexible body portion and the collection substrate.

11. The apparatus of claim 10, wherein the first distal end portion is rigid.

12. The apparatus of claim 11, wherein the case member is rigid and includes a lubricant that covers an exterior portion of the case member and wherein the case member includes a polymer and is adapted to extend a length of the vaginal cavity, and wherein the accumulator member includes cotton, cellulose, synthetic sponge material, or combinations thereof and includes a third distal end portion and a third tip section having a collection substrate at the third distal end portion, and the collection substrate including a polycarbonate layer having biologically inert mixed esters of cellulose.

13. The apparatus of claim 1, wherein the case member and the plunger member are separated from the accumulator member after placement of the accumulator member within the vaginal cavity.

14. The apparatus of claim 1, wherein the plunger member includes a second distal end portion and a second proximal end portion, the second distal end portion including a second tip section disposed within the case member, and the second tip section including an outwardly extending annual flange that has a diameter larger than a diameter of the aperture.

15. The apparatus of claim 1, wherein the collection substrate includes a layer having a plurality of collection apertures providing a passage for cell collection at an absorptive layer of the collection substrate located underneath the plurality of apertures.

16. The apparatus of claim 1, wherein the case member is substantially rigid and includes a lubricant that covers an exterior portion of the case member.

17. The apparatus of claim 16, wherein the case member is comprised of plastic polymers and is adapted to extend a length of the vaginal cavity, the accumulator member is comprised of cotton, cellulose, synthetic sponge material, or combinations thereof and including a third distal end portion and a third tip section having a collection substrate at the third distal end portion, and the collection substrate includes a polycarbonate layer having biologically inert mixed esters of cellulose.

18. The apparatus of claim 1, wherein the accumulator member is the same length as an inner cavity of the case member.

19. The apparatus of claim 1, wherein the case member includes a sleeve portion intermediate the first distal end portion and the first proximal end portion and an end wall at the first proximal end portion, and the end wall forms the aperture which is smaller than sleeve portion.

20. A method comprising: sliding an accumulator member being disposed in a case member adjacent a plunger member through a distal opening of the case member as the plunger member slides through an aperture to enable expansion of the accumulator member and placement of the accumulator member within a vaginal cavity and proximal to a cervix of a patient, the case member having a first distal end portion and a first proximal end portion, the first distal end portion having the distal opening, the first proximal end portion having the aperture, the plunger member having a second distal end portion configured to slide within the case member, the accumulator member comprising absorbent material, a third distal end portion including a frusto-conical shaped tip section, and a third tip section having a collection substrate at the third distal end portion to enable collection of cells in multiple zones during regular activity of the patient while accumulator member is in the vaginal cavity without active scraping, wherein the frusto-conical shaped tip section of the third distal end portion maintains the frusto-conical shape when positioned in the case member and outside the case member a flexible handle member being attached to the accumulator member and extending through the plunger member, the third tip section of the accumulator member including a first part emerging from the frusto-conical shaped tip section and a second part being retained in the case member by the frusto-conical shaped tip section when engaged by the plunger member; removing the accumulator member from the vaginal cavity via the flexible handle; preserving the cells in a collection receptacle; and shipping the cells in the collection receptacle.

21. The method of claim 20, wherein preserving comprises:

exposing the cells to a preservation fluid after collection.

* * * * *